United States Patent [19]

Laruelle et al.

[11] Patent Number: 4,621,088
[45] Date of Patent: Nov. 4, 1986

[54] N-ACYL DERIVATIVES OF AMINO ACIDS AND THEIR ESTERS, AND DRUGS IN WHICH THEY ARE PRESENT

[75] Inventors: Claude Laruelle, Villeneuve-Loubet; Marcel Lepant, Nice; Bernard Raynier, Cagnes sur Mer, all of France

[73] Assignee: Panmedica, Carros, France

[21] Appl. No.: 737,131

[22] Filed: May 23, 1985

[51] Int. Cl.$^4$ .................. A61K 31/33; C07D 471/04
[52] U.S. Cl. ........................... 514/300; 546/123; 546/86; 546/83; 544/127; 544/362
[58] Field of Search ............... 546/123, 86, 156, 83; 544/127, 362; 514/300

[56] References Cited

U.S. PATENT DOCUMENTS 4,024,255 5/1977 Ellis et al. ..................... 546/123

Primary Examiner—Henry R. Jiles
Assistant Examiner—J. Richter
Attorney, Agent, or Firm—Browdy and Neimark

[57] ABSTRACT

The present invention relates to new N-acyl derivatives of amino acids.

These derivatives correspond to the general formula I below:

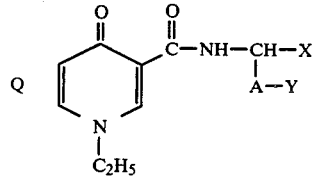

in which

A represents a linear or branched, saturated hydrocarbon radical containing from 1 to 6 carbon atoms or a saturated ring containing 6 carbon atoms, X represents a —COOH radical, a —COOAlkyl radical (alkyl from $C_1$ to $C_4$), a hydrogen atom or a —CH$_3$ group when Y is —COOH or —COOAlkyl, Y represents a —COOH radical, a —COOAlkyl radical (alkyl from $C_1$ to $C_4$), an —NH$_2$ group, an —SH group, an —SCH$_3$ group, a —NH—CH(=NH)—NH$_2$ group, a substituted or unsubstituted phenyl group, an indolin-3-yl group or a 5-hydroxyindolin-3-yl group, and Q represents an optionally substituted aromatic ring or an optionally substituted heterocycle containing 1 or 2 nitrogen atoms.

Drugs having an antiallergic action.

12 Claims, No Drawings

N-ACYL DERIVATIVES OF AMINO ACIDS AND THEIR ESTERS, AND DRUGS IN WHICH THEY ARE PRESENT

The present invention relates to new N-acyl derivatives of amino acids and their esters, to the process for their preparation and to drugs in which these derivatives are present.

Derivatives of 4-oxoquinolines and 4-oxonaphthyridines are known as constituents of drugs which have a powerful antibacterial or antiallergic action. This group includes, for example, antibacterial agents such as nalidixic acid, 1-ethyl-6-fluoro-4-oxo-7-(piperazin-1-yl)-1-dihydro-1,8-naphthyridine-3-carboxylic acid (enoxacin), pipemidic acid and oxolinic acid, or an antiallergic agent such as, for example, the naphthyridine derivative described in U.S. Pat. No. 4 303 661.

In pursuing the synthesis and study of this extremely promising group, the Applicant Company has been able to develop a new series of derivatives possessing particularly valuable pharmacological properties, especially an antiallergic action, an action on the central nervous system and an action on the cardiovascular system.

The present invention relates to the 1-ethyl-pyridin-4-one-3-carboxylic derivatives of amino acids and their esters corresponding to the general formula I below:

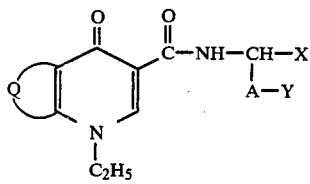

in which
- A represents: a linear or branched, saturated hydrocarbon radical containing from 1 to 6 carbon atoms or a saturated ring containing 6 carbon atoms,
- X represents: a —COOH radical, a —COOAlkyl radical (alkyl from $C_1$ to $C_4$), a hydrogen atom or a —CH$_3$ group when Y is —COOH or —COOAlkyl,
- Y represents: a —COOH radical, a —COOAlkyl radical (alkyl from $C_1$ to $C_4$), an —NH$_2$ group, an —SH group, an —SCH$_3$ group, a —NH—CH(=NH)—NH$_2$ group, a substituted or unsubstituted phenyl group, an indolin-3-yl group or a 5-hydroxyindolin-3-yl group, and
- Q represents: an optionally substituted aromatic ring or an optionally substituted heterocycle containing 1 or 2 nitrogen atoms.

The present invention also relates to a process for the manufacture of derivatives according to the present invention, which comprises reacting a reactive derivative of the substituted 1-ethylpyridin-4-one-3-carboxylic acid with an amino acid ester in a suitable solvent, it then being possible, if appropriate, for the resulting ester to be unblocked by conventional saponification, the reactions taking place in solvents suitable for N-acylations.

In an advantageous embodiment of the process forming the subject of the present invention, any reactive groups other than the NH$_2$—group of the amino acid ester used have been blocked.

These protected groups are then unblocked by the techniques normally used in peptide synthesis.

In another advantageous embodiment of the process forming the subject of the present invention, the amine group of the amino acid ester used is in the form of its phosphorazo compound.

Apart from the foregoing provisions, the invention also includes other provisions which will become apparent from the following description.

The invention will be understood more clearly with the aid of the following additional description, which refers to a pharmacological report and practical examples of the process forming the subject of the present invention.

It must be clearly understood, however, that these practical examples and the corresponding descriptive sections are given solely in order to illustrate the subject of the invention.

EXAMPLE 1

Preparation of Ethyl 3-N-(1-Ethyl-1,4-Dihydro-6,7-Methylenedioxy-4-Oxoquinoline-3-Carbonyl)Aminobutyrate 140 mmol of triethylamine diluted in dimethylformamide are added to a suspension of 28.25 g (108 mmol) of 1-ethyl-1,4-dihydro-6,7-methylenedioxy-4-oxoquinoline-3-carboxylic acid in 500 ml of dimethylformamide, and 140 mmol of ethyl chloroformate are then added slowly at 0° C. After stirring for two hours at ambient temperature, 15.10 g (115 mmol) of ethyl 3-aminobutyrate diluted in 80 ml of DMF are added. The mixture is stirred at ordinary temperature for several days until the condensation reaction has ended.

The mixture is then evaporated in vacuo, the residue is taken up with chloroform and the organic layer is washed successively with dilute sodium hydroxide solution, water, normal hydrochloric acid and finally water. After evaporation of the solvent, the residue is purified by chromatography on silica in a chloroform/acetone system to give the title derivative with a yield of 50% and a melting point of 180° C.

EXAMPLE 2

3-N-(1-Ethyl-1,4-Dihydro-6,7-Methylenedioxy-4-Oxoquinoline-3-Carbonyl)Aminobutyric Acid 13.6 g (36.4 mmol) of the ester prepared according to Example 1 are suspended in 150 ml of ethanol and 90 ml of normal sodium hydrodie solution. The suspension is stirred at ordinary temperature until the saponification has ended, i.e. for about 20 hours. The ethanol is then evaporated off, the residue is taken up with water, the mixture is treated with carbon black and the product is precipitated with dilute hydrochloric acid. After filtration, washing with water and drying, the title derivative is obtained in the form of a white crystalline product with a melting point of 295° C. and a yield of 80%. Thin layer chromatography of this product on a silica plate in the system chloroform 25/acetone 7 gives a spot of Rf=0.4, which is visible under UV.

EXAMPLE 3

Tert.-Butyl 4-N-(1-Ethyl-1,4-Dihydro-6,7-Methylenedioxy-4-Oxoquinoline-3-Carbonyl)Aminobutyrate 12.7 g (80 mmol) of tert.-butyl 4-aminobutyrate are dissolved in 500 ml of pyridine, and 22.36 g (80 mmol) of the chloride of 1-ethyl-1,4-dihydro-6,7-methylenedioxy-4-oxoquinoline-3-carboxylic acid are then added.

After heating for 8 hours at about 100° C., the mixture is stirred for 20 hours at ordinary temperature and evaporated in vacuo at low temperature, and the residue is then taken up with chloroform; after several washings with dilute HCl, normal sodium hydroxide solution and water, the organic layer is evaporated. The product is then purified by chromatography on silica in a chloroform/methanol system. This gives the title derivative in the form of white crystals with a melting point of 192° C., which, in TLC on a silica gel plate, give a single spot of Rf=0.55 (UV) in the solvent system chloroform 30/methanol 2.

EXAMPLE 4

4-N-(1-Ethyl-1,4-Dihydro-6,7-Methylenedioxy-4-Oxoquinoline-3-Carbonyl)Aminobutyric Acid 10.5 g (26.2 mmol) of the ester prepared according to Example 3 are suspended in 20 ml of glacial acetic acid, and 60 ml of acetic acid saturated with hydrochloric acid beforehand are then added at ordinary temperature. The reaction vessel is hermetically stoppered and the mixture is stirred for 2 hours. Part of the excess hydrogen chloride is subsequently evaporated off and the mixture is then diluted with ether to precipitate the crude product. After dissolution in excess dilute sodium hydroxide solution, treatment with carbon black and reprecipitation with dilute HCl, the precipitate is filtered off and washed. This gives the title derivative with a yield of 82% in the form of white crystals with a melting point of 230° C. In TLC on a silica gel plate in the system n-butanol 8/acetic acid 1/water 1, the product gives a spot of Rf=0.65.

EXAMPLE 5

Benzyl 3-N-(1-Ethyl-1,4-Dihydro-6,7-Methylenedioxy-4-Oxoquinoline-3-Carbonyl)Aminopropionate 18.55 g (71 mmol) of 1-ethyl-1,4-dihydro-6,7-methylenedioxy-4-oxoquinoline-3-carboxylic acid are suspended in 300 ml of dimethylformamide, 92 mmol of triethylamine dissolved in a small quantity of dimethylformamide are added and 10 g (92 mmol) of ethyl chloroformate are then run in at 0° C. After one hour at ordinary temperature, a solution of 80 mmol of benzyl 3-aminopropionate in 100 ml of DMF is run in and the reaction mixture is stirred for 24 hours at ambient temperature. After evaporation of the solvent at low temperature, the residue is taken up with chloroform and the mixture is washed successively with dilute hydrochloric acid, dilute sodium hydroxide solution and then water. The solvent is evaporated off and the product is purified by chromatography on a silica column with a chloroform/acetone mixture. This gives 65% of the title derivative in the form of crystals with a melting point of 180° C., which, in TLC on a silica plate in the system chloroform 30/methanol 1, give a single spot of Rf=0.75.

EXAMPLE 6

3-N-(1-Ethyl-1,4-Dihydro-6,7-Methylenedioxy-4-Oxoquinoline-3-Carbonyl)Aminopropionic Acid 10.95 g (26 mmol) of the ester prepared in Example 5 are suspended in 150 ml of ethanol, 65 ml of normal sodium hydroxide solution are added and the mixture is stirred at ordinary temperature until total solubilization has taken place. It is treated with carbon black and then acidified with dilute hydrochloric acid, and the precipitate formed as filtered off, washed with water and dried. This gives the title derivative with a yield of 98% in the form of white crystals with a melting point of 290° C., which, in TLC on silica in the system n-butanol 8/acetic acid 1/water 1, give a single spot of Rf=0.60.

EXAMPLE 7

Ethyl 6-N-(1-Ethyl-1,4-Dihydro-6,7-Methylenedioxy-4-Oxoquinoline-3-Carbonyl)Aminohexanoate 39.72 g (0.12 mol) of ethyl 6-aminohexanoate are dissolved in 500 ml of pyridine, and 0.12 mol of the chloride of 1-ethyl-1,4-dihydro-6,7-methylenedioxy-4-oxoquinoline-3-carboxylic acid is then added at 0° C. The mixture is left to return to ambient temperature and then heated at 100° C. for 15 hours; after evaporation of the solvent at low temperature, the residue is taken up with dilute hydrochloric acid and the mixture is extracted with chloroform. After washing with dilute hydrochloric acid and dilute sodium hydroxide solution and then with water, the organic layer is evaporated to dryness. The residue is taken up with ether and then recrystallized from isopropyl alcohol. This gives the title derivative in the form of white crystals with a melting point of 130° C., which, in TLC on a silica plate in the system toluene 10/ethyl formate 10/formic acid 1, give a single spot of Rf=0.40.

EXAMPLE 8

6-N-(1-Ethyl-1,4-Dihydro-6,7-Methylenedioxy-4-Oxoquinoline-3-Carbonyl)Aminohexanoic Acid 12.15 g (30.2 mmol) of the ester obtained in Example 7 are suspended in 60 ml of ethanol, and 26 ml of normal sodium hydroxide solution are then added. After stirring for 15 hours, dissolution is complete, 50 ml of water are added and the mixture is then acidified with dilute hydrochloric acid. The precipitate formed is filtered off, washed and dried; this gives the title derivative in the pure state in the form of white crystals with a melting point of 210° C., which, in TLC on a silica plate in the system toluene 10/ethyl formate 10/formic acid 1, give a single spot of Rf=0.25.

EXAMPLE 9

Diethyl (L)-N-(1-Ethyl-1,4-Dihydro-6,7-Methylenedioxy-4-Oxoquinoline-3-Carbonyl)Glutamate 23 g (0.13 mol) of diethyl glutamate are dissolved in 750 ml of pyridine, and 0.13 mol of the chloride of 1-ethyl-1,4-dihydro-6,7-methylenedioxy-4-oxoquinoline-3-carboxylic acid is then added at 0° C. The mixture is heated at 100° C. for 15 hours, a small amount of insoluble material is filtered off hot and the solution is then evaporated. The residue is taken up with iced dilute hydrochloric acid and the mixture is extracted with chloroform. The organic solution is washed in the usual manner and then, after evaporation, chromatographed on a silica column. This gives the title derivative in the form of white crystals with a melting point of 159° C., which, in TLC on a silica plate in the system chloroform 25/acetone 5, give a signle spot of Rf=0.45.

EXAMPLE 10

(L)-N-(1-Ethyl-1,4-Dihydro-6,7-Methylenedioxy-4-Oxoquinoline-3-Carbonyl)Glutamic Acid 18.50 g (32 mmol) of the ester described in Example 9 are suspended in 100 ml of ethanol an 98 ml of normal sodium hydroxide solution. The suspension is stirred at ordinary temperature until total solubilization has taken place, and then diluted with water and treated with carbon black, and the product is precipitated with dilute hydrochloric acid. After filtration, washing with water and drying, the title derivative is obtained in the form of white crystals with a melting point of 237° C., which, in TLC on a silica plate in the system butanol 8/acetic acid 1/water 1, give a single spot of Rf=0.45.

EXAMPLE 11

Diethyl (L)-N-(1-Ethyl-1,4-Dihydro-6,7-Methylenedioxy-4-Oxoquinoline-3-Carbonyl)Aspartate 115 mmol of diethyl (L)-aspartate are dissolved in 400 ml of pyridine, and 32.15 g (115 mmol) of the chloride of 1-ethyl-1,4-dihydro-6,7-methylenedioxy-4-oxoquinoline-3-carboxylic acid are then added slowly at about +5° C. The mixture is then heated at 100° C. for 5 hours, after which it is stirred at ordinary temperature for 16 hours. It is then evaporated under reduced pressure and the residue is taken up with 400 ml of normal hydrochloric acid. The precipitate formed is filtered off, washed with water and dried.

The product is then purified by chromatography on a silica column in a chloroform/acetone system to give the title derivative in the form of white crystals with a melting point of 148° C., which, in TLC on a silica plate in the system chloroform 20/acetone 5, give a single spot of Rf=0.45.

EXAMPLE 12

(L)-N-(1-Ethyl-1,4-Dihydro-6,7-Methylenedioxy-4-Oxoquinoline-3-Carbonyl)Aspartic Acid 21.6 g (50 mmol) of the diester described in Example 11 are suspended in 100 ml of ethanol and 150 ml of normal sodium hydroxide solution. The suspension is stirred for 24 hours at ordinary temperature, treated with carbon black and then acidified with dilute hydrochloric acid. The precipitate formed is filtered off, washed and dried. This gives the title derivative with a yield of 90% in the form of white crystals with a melting point of 221° C., which, in TLC on a silica plate in the system n-butanol 8/acetic acid 1/water 1, give a single spot of Rf=0.30.

EXAMPLE 13

Ethyl 4-N-(1-Ethyl-1,4-Dihydro-6,7-Methylenedioxy-4-Oxoquinoline-3-Carbonyl)Aminomethylcyclohexanecarboxylate 14.2 g (140 mmol) of triethylamine and then 14.8 g (137 mmol) of ethyl chloroformate are added to a suspension of 29.5 g (113 mmol) of 1-ethyl-1,4-dihydro-6,7-methylenedioxy-4-oxoquinoline-3-carboxylic acid in 450 ml of dimethylformamide. After stirring for 2 hours at ambient temperature, 113 mmol of ethyl 4-aminomethylcyclohexanecarboxylate are added. The suspension is stirred at ambient temperature for several days until the reaction has ended. The major part of the solvent is evaporated off in vacuo, the residue is then taken up with chloroform and the mixture is washed in the usual manner. After evaporation of the solvent, the crude product is purified by chromatography on silica with a chloroform/acetone mixture. This gives the title derivative in the pure state (melting point=214° C.). TLC on silica in the system chloroform 30/isopropanol 1.5 gives a single spot of Rf=0.45.

EXAMPLE 14

4-N-(1-Ethyl-1,4-Dihydro-6,7-Methylenedioxy-4-Oxoquinoline-3-Carbonyl)Aminomethylcyclohexanecarboxylic Acid 3.43 g (8 mmol) of the above ester are suspended in 35 ml of ethanol, 20 ml of normal sodium hydroxide solution and 20 ml of water. After stirring for 15 hours at ambient temperature, the suspension is acidified with dilute hydrochloric acid and filtered and the precipitate is washed. After drying, the title derivative is obtained in the pure state with a yield of 72% (melting point=301° C.). TLC on silica in the system chloroform 30/isopropanol 1.5 gives a single spot of Rf=0.15.

EXAMPLE 15

Ethyl 3-N-(1-Ethyl-1,4-Dihydro-7-Methyl-4-Oxo-1,8-Naphthyridine-3-Carbonyl)Aminopropionate 6.90 g (50 mmol) of phosphorus trichloride are added to a solution of ethyl 3-aminopropionate hydrochloride (15.3 g; 0.1 mol) in 400 ml of pyridine. After stirring for 2 hours at ambient temperature, 23.1 g (0.1 mol) of 1-ethyl-1,4-dihydro-7-methyl-4-oxo-1,8-naphthyridine-3-carboxylic acid are added and the mixture is heated at 105°/115° C. for 16 hours. After cooling, the solvent is evaporated off under reduced pressure and the residue is then taken up with normal hydrochloric acid. The aqueous solution is extracted with chloroform and the chloroform extract is washed with dilute hydrochloric acid, then with dilute sodium hydroxide solution and finally with water. After evaporation of the solvent, the residue is taken up with ether and then with hot ethanol. After filtration and drying, the title derivative is obtained in the form of white crystals with a melting point of 178° C., which, in TLC on a silica plate in the system toluene 10/ethyl formate 10/formic acid 1, give a single spot of Rf=0.50.

EXAMPLE 16

3-N-(1-Ethyl-1,4-Dihydro-7-Methyl-4-Oxo-1,8-Naphthyridine-3-Carbonyl)Aminopropionic Acid By hydrolysis of the ethyl ester:

0.1 mol of the ester described in the above example is suspended in 500 ml of ethanol and 150 ml of normal sodium hydroxide solution and the suspension is stirred at ordinary temperature for 15 hours. The ethanol is evaporated off under reduced pressure, the residue is diluted with water and the product is then precipitated by acidification. After filtration, washing with water and drying, the title derivative is obtained in the form of white crystals with a melting point of 252° C. and a yield of 70%. TLC of the derivative on silica in the system toluene 10/ethyl formate 10/formic acid 1 gives a single spot of Rf=0.30.

By hydrolysis of the benzyl ester:

Benzyl 3-N-(1-Ethyl-1,4-Dihydro-7-Methyl-4-Oxo-1,8-Naphthyridine-3-Carbonyl)Aminopropionate.

45.7 g (0.13 mol) of benzyl 3-aminopropionate paratoluenesulfonate are dissolved in 450 ml of pyridine, and 9 g of phosphorus trichloride (65 mmol) are then added at about +5° C.

After 2 hours at ordinary temperature, 30.2 g (0.13 mol) of 1-ethyl-1,4-dihydro-7-methyl-4-oxo-1,8-naphthyridine-3-carboxylic acid are added and the mixture is heated at 105°–110° C. for 15 hours. After a treatment identical to that of the above ethyl ester, the title derivative is obtained with a melting point of 157° C. and a yield of 90%.

Hydrolysis of the benzyl ester:

0.1 mol of the ester described above is suspended in 500 ml of ethanol and 150 ml of normal sodium hydroxide solution. After stirring for 15 hours at ambient temperature, the ethanol is evaporated off under reduced pressure and, after dilution with water, the mixture is acidified to precipitate the acid form, which is identical in every respect to the product obtained by hydrolysis of the ethyl ester.

EXAMPLE 17

Ethyl
3-N-(1-Ethyl-1,4-Dihydro-7-Methyl-4-Oxo-1,8-Naphthyridine-3-Carbonyl)Aminobutyrate 13.1 g (0.1 mol) of ethyl 3-aminobutyrate are dissolved in 400 ml of pyridine, and 6.9 g (50 mmol) of phosphorus trichloride are then added at about 10°. After stirring for 2 hours at ambient temperature, 23.2 g of 1-ethyl-1,4-dihydro-7-methyl-4-oxo-1,8-naphthyridine-3-carboxylic acid are added. The mixture is kept at 100°–105° C. for 15 hours, the solvent is evaporated off under reduced pressure and then, by extraction with chloroform and washing in the usual manner, the title derivative is obtained in the pure state with a melting point of 107° C. after chromatography on silica with a chloroform/acetone mixture. TLC (silica: chloroform 30/methanol 2—Rf=0.60).

EXAMPLE 18

3-N-(1-Ethyl-1,4-Dihydro-7-Methyl-4-Oxo-1,8-Naphthyridine-3-Carbonyl)Aminobutyric Acid 4.7 g (13.6 mmol) of the ester obtained above are suspended in 60 ml of ethanol and 27 ml of normal sodium hydroxide solution. The suspension is stirred for 16 hours at ordinary temperature, the ethanol is evaporated off, the residue is diluted with water and the product is then precipitated in the cold with dilute hydrochloric acid. After filtration, washing and drying, the title derivative is obtained in the pure state in the form of white crystals with a melting point of 254° C. and a yield of 93% (TLC on silica in n-butanol 80/water 10/acetic acid 1 gives a single spot of Rf=0.80).

EXAMPLE 19

Tert.-Butyl
4-N-(1-Ethyl-1,4-Dihydro-7-Methyl-4-Oxo-1,8-Naphthyridine-3-Carbonyl)Aminobutyrate 13.5 g (85 mmol) of tert.-butyl 4-aminobutyrate are dissolved in 250 ml of pyridine, and 5.5 g (40 mmol) of phosphorus trichloride diluted in a small quantity of pyridine are then run in. The mixture is stirred for 2 hours at ambient temperature and 18.2 g of 1-ethyl-1,4-dihydro-7-methyl-4-oxo-1,8-naphthyridine-3-carboxylic acid are then added. After heating at 105°/115° C. for 7 hours, the solvent is evaporated off under reduced pressure and the residue is taken up with chloroform.

After the chloroform extract has been washed in the usual manner, the crude residue from solvent evaporation is purified by chromatography on a silica column with a chloroform/methanol mixture. This gives the title derivative in the form of white crystals with a melting point of 119° C. (TLC on silica in the mixture chloroform 20/methanol 0.4 gives a single spot of Rf=0.60).

EXAMPLE 20

4-N-(1-Ethyl-1,4-Dihydro-7-Methyl-4-Oxo-1,8-Naphthyridine-3-Carbonyl)Aminobutyric Acid 6 g (16 mmol) of the ester prepared in the above examples are suspended in 40 ml of glacial acetic acid saturated with hydrogen chloride. After stirring for 2 hours, the suspension is evaporated under reduced pressure and the residue is taken up with ether. The product is purified by dissolution in an alkaline medium, treatment with carbon black and reprecipitation with dilute hydrochloric acid. After filtration, washing and drying, the title derivative is obtained with a yield of 90% (melting point=178° C.). TLC on silica in the system toluene 10/ethyl formate 10/formic acid 1 gives a single spot of Rf=0.40.

EXAMPLE 21

Ethyl
6-N-(1-Ethyl-1,4-Dihydro-7-Methyl-4-Oxo-1,8-Naphthyridine-3-Carbonyl)Aminohexanoate 39.8 g (0.12 mol) of ethyl 6-aminohexanoate are dissolved in 600 ml of pyridine, and 8.3 g (60 mmol) of phosphorus trichloride are then run in. After stirring for 2 hours at ambient temperature, 27.9 g (0.12 mol) of 1-ethyl-1,4-dihydro-7-methyl-4-oxo-1,8-naphthyridine-3-carboxylic acid are added and the mixture is then heated at 100° C. for 16 hours. After evaporation under reduced pressure, the residue is taken up with dilute hydrochloric acid and the mixture is extracted with chloroform. The organic extract is washed in the usual manner.

After evaporation to dryness under reduced pressure, the residue is recrystallized from isopropyl alcohol. This gives the title derivative with a melting point of 113° C. TLC on silica in the system toluene 10/ethyl formate 10/formic acid 1 gives a single spot of Rf=0.50.

EXAMPLE 22

6-N-(1-Ethyl-1,4-Dihydro-7-Methyl-4-Oxo-1,8-Naphthyridine-3-Carbonyl)Aminocaproic Acid 19.5 g (52 mmol) of the ester prepared in the above example are suspended in 90 ml of ethanol and 50 ml of 2N sodium hydroxide solution. After stirring for 18 hours, the suspension is diluted with water, treated with carbon black and acidified with concentrated hydrochloric acid. After washing and drying, the precipitate is the title derivative with a melting point of 163° C. TLC on silica in the system toluene 10/ethyl formate 10/formic acid 1 gives a single spot of Rf=0.40.

EXAMPLE 23

Ethyl
4-N-(1-Ethyl-1,4-Dihydro-7-Methyl-4-Oxo-1,8-Naphthyridine-3-Carbonyl)Aminomethylcyclohexanecarboxylate 16.6 g (75 mmol) of ethyl 4-aminomethylcyclohexanecarboxylate are dissolved in 300 ml of pyridine, and 5.2 g (37 mmol) of phosphorus trichloride are added, followed, after 2 hours at ordinary temperature, by 17.4 g (75 mmol) of 1-ethyl-1,4-dihydro-7-methyl-4-oxo-1,8-naphthyridine-3-carboxylic acid. After 15 hours at 115°/120° C., the solvent is evaporated off, the residue is taken up with normal hydrochloric acid, the mixture is extracted with chloroform and then, after the usual treatment, the crude product is recrystallized from isopropanol. This gives the title derivative with a yield of 50% in the form of white crystals with a melting point of 165° C. TLC on silica in the system chloroform 60/acetone 10 gives a single spot of Rf=0.55.

EXAMPLE 24

4-N-(1-Ethyl-1,4-Dihydro-7-Methyl-4-Oxo-1,8-Naphthyridine-3-Carbonyl)Aminomethylcyclohexanecarboxylic Acid 12 g (30 mmol) of the ester obtained in the above example are suspended in 120 ml of ethanol and 60 ml of normal sodium hydroxide solution. After stirring for 18 hours at ambient temperature, the ethanol is evaporated off, the residue is diluted with water and the acid form is precipitated with dilute hydrochloric acid. After filtration, washing and drying, the title derivative is obtained pure in the form of white crystals with a melting point of 259° C. and a yield of 92%. TLC on silica in the system chloroform 60/acetone 10 gives a single spot of Rf=0.40.

EXAMPLE 25

Dimethyl
(L)-N-(1-Ethyl-1,4-Dihydro-7-Methyl-4-Oxo-1,8-Naphthyridine-3-Carbonyl)Aspartate 8.50 g (58 mmol) of dimethyl (L)-aspartate are dissolved in 220 ml of pyridine, and 4 g (29 mmol) of phosphorus trichloride are added, followed, after stirring for 2 hours at ambient temperature, by 58 mmol of 1-ethyl-1,4-dihydro-7-methyl-4-oxo-1,8-naphthyridine-3-carboxylic acid. The mixture is heated under reflux for 8 hours, after which the solvent is evaporated off, the residue is taken up with 400 ml of hydrochloric acid and the mixture is extracted with chloroform. After washing of the organic extract by the usual techniques and evaporation of the chloroform, the crude residue is purified by chromatography on silica with a chloroform/acetone mixture This gives the title derivative in the form of white crystals with a melting point of 135° C. TLC on silica in chloroform 80/acetone 10 gives a single spot of Rf=0.55.

EXAMPLE 26

Diethyl
(L)-N-(1-Ethyl-1,4-Dihydro-7-Methyl-4-Oxo-1,8-Naphthyridine-3-Carbonyl)Aspartate The procedure of the above example is followed using 58 mmol of diethyl (L)-aspartate to give the title derivative with a yield of 77% and a melting point of 103° C. TLC on silica in the system benzene 8/acetone 2 gives a single spot of Rf=0.70.

EXAMPLE 27

(L)-N-(1-Ethyl-1,4-Dihydro-7-Methyl-4-Oxo-1,8-Naphthyridine-3-Carbonyl)Aspartic Acid 24.2 g (60 mmol) of the above ester are suspended in 125 ml of ethanol and 180 ml of normal sodium hydroxide solution and the suspension is stirred at ordinary temperature for 18 hours. It is then acidified with dilute hydrochloric acid and the precipitate is filtered off, washed and dried. This gives the title derivative in the form of white crystals with a melting point of 207° C. and a yield of 70%. TLC on silica in the system n-butanol 8/water 1/acetic acid 1 gives a single spot of Rf=0.40.

EXAMPLE 28

Diethyl
(L)-N-(1-Ethyl-1,4-Dihydro-7-Methyl-4-Oxo-1,8-Naphthyridine-3-Carbonyl)Glutamate 4.8 g (20 mmol) of diethyl (L)-glutamate hydrochloride are dissolved in 40 ml of pyridine, and 1.4 g (10 mmol) of phosphorus trichloride diluted in 15 ml of pyridine are then added. The mixture is stirred for one hour at ordinary temperature and 4.65 g (20 mmol) of 1-ethyl-1,4-dihydro-7-methyl-4-oxo-1,8-naphthyridine-3-carboxylic acid are then added.

After refluxing for 7 hours, the mixture is concentrated under reduced pressure, the concentrate is taken up with chloroform and the mixture is washed in the usual manner. After evaporation to dryness, the title derivative is obtained in the pure state with a melting point of 103° C. TLC on silica in the system benzene 8/methanol 2 gives a single spot of Rf=0.80.

EXAMPLE 29

(L)-N-(1-Ethyl-1,4-Dihydro-7-Methyl-4-Oxo-1,8-Naphthyridine-3-Carbonyl)Glutamic Acid 4.2 g (10 mmol) of the above ester are suspended in 20 ml of ethanol and 30 ml of normal sodium hydroxide solution. After stirring for a few hours at ordinary temperature, the suspension is acidified with dilute hydrochloric acid. The precipitate is filtered off, washed with water and then taken up with an ethanol/ester mixture. The insoluble material after filtration and drying represents the title derivative in the pure state with a melting point of 220° C. and a yield of 70%. TLC on silica in the system n-butanol 8/acetic acid 1/water 1 gives a single spot of Rf=0.60.

PHARMACOLOGICAL REPORT

The products according to the invention all possess antiallergic properties. Thus, when injected at doses of 12.5 and 25 mg/kg, they have protective properties towards the anaphylactic reaction triggered by the intravenous injection of ovalbumin into sensitized rats. When injected at doses of between 5 and 50 mg/kg, the derivatives according to the invention induce an antihypertensive effect comparable to that of alphamethyldopa in spontaneously hypertensive rats. The positive inotropic cardiac activity measured on isolated guinea-pig heart is greater than that of amrinone. Finally, the bronchodilatatory activities of the derivatives according to the invention, tested on the isolated organ, are comparable to that of aminophylline. Furthermore, the toxicities of the derivatives of the present invention, measured by the $LD_{50}$ technique on mice, are low and the $LD_{50}$ values are generally greater than 2000 mg/kg, administered orally.

The products according to the invention can be administered to animals in the conventional manner, either by themselves or in combination with other therapeutic agents. The dosage of the form administered varies according to the pharmacodynamic characteristics of the product in question and the method of administration. This dosage also varies according to the age of the patient and the nature and extent of the symptoms and according to the desired effects.

Usually, a daily dose of active product can be between 5 and 20 milligrams per kilogram of body weight.

The active principle can be administered orally in solid galenic forms such as tablets, capsules or powders, or in liquid forms such as syrups or suspensions; it can also be administered parenterally in solution in a suitable sterile solvent.

As is apparent from the foregoing description, the invention is in no way limited to those methods of implementation, embodiments and methods of application which have now been described more explicitly; on the contrary, it includes all the variants thereof which may occur to those skilled in the art, without exceeding the framework or the scope of the present invention.

What is claimed is:

1. 1-Ethylpyridin-4-one-3-carboxylic derivatives of amino acids and pharmaceutically acceptable salts thereof, corresponding to formula I below:

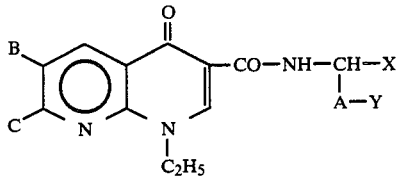

in which A represents: a linear or branched, saturated hydrocarbon radical containing from 1 to 6 carbon atoms or cyclohexyl, X represents: a —COOH radical, a —COOAlkyl radical (alkyl from $C_1$ to $C_4$), a hydrogen atom or a —$CH_3$ group when Y is —COOH or —COOAlkyl, Y represents: a —COOH radical, a —COOAlkyl radical (alkyl from $C_1$ to $C_4$), an —$NH_2$ group, an —SH group, an —$SCH_3$ group, a —NH—CH(=NH)—$NH_2$ group, a mono- or di-OH substituted or unsubstituted phenyl group, an indolin-3-yl group or a 5-hydroxyindolin-3-yl group, B represents: a —$CH_3$ radical, a $CF_3$ radical, an $OCH_3$ radical, a hydrogen atom or a halogen atom, and C represents: an —$OCH_3$ group, an ethoxy radical, an alkyl group from $C_1$ to $C_4$, a hydrogen atom, a diethyl or dimethyl aminoethylamino group, or a diethyl or dimethylamino radical.

2. Addition salts of the compounds as claimed in claim 1 with pharmaceutically acceptable acids wherein X or Y is an amine group.

3. Addition salts of the compounds as claimed in claim 1 with pharmaceutically acceptable bases wherein X or Y is COOH.

4. The derivatives as claimed in claim 1 in which Q and the pyridone together form the 1-ethyl-1,4-dihydro-6,7-methylenedioxy-4-oxoquinolin-3-yl derivative.

5. The derivatives as claimed in claim 1 in which Q and the pyridone together form the 1-ethyl-1,4-dihydro-7-methyl-4-oxo-1,8-naphthyridin-3-yl derivative.

6. A derivative as claimed in claim 1, which consists of 4-N-(1-ethyl-1,4-dihydro-6,7-methylenedioxy-4-oxoquinoline-3-carbonyl)aminobutyric acid.

7. A derivative as claimed in claim 1, which consists of diethyl (L)-N-(1-ethyl-1,4-dihydro-6,7-methylenedioxy-4-oxoquinoline-3-carbonyl)glutamate.

8. A derivative as claimed in claim 1, which consists of diethyl (L)-N-(1-ethyl-1,4-dihydro-6,7-methylenedioxy-4-oxoquinoline-3-carbonyl)aspartate.

9. A derivative as claimed in claim 1, which consists of diethyl (L)-N-(1-ethyl-1,4-dihydro-7-methyl-4-oxo-1,8-naphthyridine-3-carbonyl)aspartate.

10. A derivative as claimed in claim 1, which consists of diethyl (L)-N-(1-ethyl-1,4-dihydro-7-methyl-4-oxo-1,8-naphthyridine-3-carbonyl)glutamate.

11. A pharmaceutical composition comprising an antihistaminically, bronchiospasmolitically or inotropically effective amount of at least one compound as claimed in claim 6.

12. A derivative according to claim 1 wherein B represents $CH_3$ or H and C represents $CH_3$ or H.

* * * * *